United States Patent [19]

Noda et al.

[11] 4,009,166
[45] Feb. 22, 1977

[54] PYRIDO(2,3-d) PYRIMIDINONES

[75] Inventors: Kanji Noda, Chikushino; Akira Nakagawa, Tosu; Toshiharu Motomura, Tosu; Satoru Miyata, Tosu; Hiroyuki Ide, Fukuoka, all of Japan

[73] Assignee: Hisamitsu Pharmaceutical Co., Inc., Japan

[22] Filed: June 2, 1975

[21] Appl. No.: 582,889

[30] Foreign Application Priority Data

June 12, 1974 Japan .............................. 49-67791
July 5, 1974 Japan .............................. 49-80367

[52] U.S. Cl. ................ 260/256.4 F; 260/256.5 R; 424/251
[51] Int. Cl.² ...................... C07D 471/04
[58] Field of Search ............................ 260/256.4 F

[56] References Cited
UNITED STATES PATENTS 3,853,898  12/1974  Hardtmann et al. ........ 260/256.4 F
3,873,545  3/1975   Osselaere et al. ............ 260/256.4 F
3,922,275  11/1975  Noda et al. ................. 260/256.4 F Primary Examiner—Donald G. Daus
Assistant Examiner—James H. Turnipseed
Attorney, Agent, or Firm—Browdy and Neimark

[57] ABSTRACT

The compounds of the present invention can be represented by the following formula:

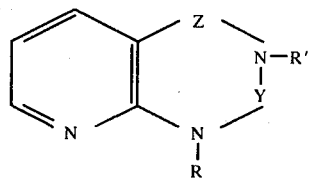

wherein R is selected from the group consisting of phenyl and substituted phenyl; R' is selected from the group consisting of hydrogen, lower alkyl, unsaturated lower alkyl, substituted lower alkyl, lower alkoxycarbonyl and aralkyl; Y and Z are selected from the group consisting of carbonyl and methylene, but Y and Z are always dissimilar.

The compounds of the present invention possess a high degree of pharmacological activities such as anti-inflammatory, anti-ulcerative, analgetic, antipyretic, antihistaminic and central nervous system depressive activities, and certain of them are useful as new anti-inflammatory agents, analgesics and central nervous system depresssants.

30 Claims, No Drawings

PYRIDO(2,3-d) PYRIMIDINONES

DETAILED DESCRIPTION

The present invention relates to the compounds represented by the general formula [A]:

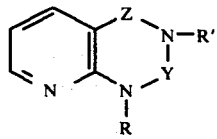

wherein R is selected from the group consisting of phenyl and substituted phenyl; R' is selected from the group consisting of hydrogen, lower alkyl, unsaturated lower alkyl, substituted lower alkyl, lower alkoxycarbonyl and aralkyl; Y and Z are selected from the group consisting of carbonyl and methylene, but Y and Z are always dissimilar.

More particularly, R is selected from the group consisting of
1. phenyl and
2. substituted phenyl with one or two substituents which include halogen, lower alkyl, lower alkoxy, nitro and trifluoromethyl;

R' is selected from the group consisting of
1. hydrogen,
2. lower alkyl,
3. lower alkenyl,
4. lower alkynyl,
5. aralkyl,
6. substituted lower alkyl with halogen, hydroxyl, lower alkoxy, lower alkanoyloxy, lower cycloalkyl, carboxyl and di(lower alkyl)amino and
7. lower alkoxycarbonyl;

Y and Z are selected from the group consisting of carbonyl and methylene, but Y and Z are always dissimilar.

All of the compounds of the present invention possess at least one of such pharmacological activities as anti-inflammatory, anti-ulcerative, analgetic, antipyretic, antihistaminic and central nervous system depressive activities as well as low toxicity, and most of them possess more than one of the said activities. It is to be noted, therefore, that certain of the compounds within the scope of the present invention are useful as new analgesics, anti-inflammatory agents and central nervous system depressants.

The compounds of the present invention can be represented by the general formula I or II:

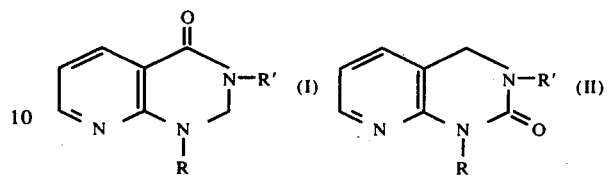

wherein R is selected from the group consisting of phenyl, halophenyl, dihalophenyl, tolyl, xylyl, nitrophenyl, halotolyl and trifluoromethylphenyl; R' is selected from the group consisting of hydrogen, lower alkyl having from one to 6 carbon atoms, lower alkenyl having from 3 to 5 carbon atoms, propargyl, cyclopropylmethyl, lower haloalkyl having from one to 3 carbon atoms, lower trihaloalkyl having from 1 to 3 carbon atoms, acetoxyethyl, lower hydroxyalkyl having from 2 to 3 carbon atoms, lower alkoxyalkyl having from 2 to 4 carbon atoms, carboxymethyl, dialkylaminoalkyl having from 4 to 6 carbon atoms, lower alkoxycarbonyl having from 2 to 3 carbon atoms and benzyl.

The compounds disclosed herein can be prepared in high yields by one of eight basic routes as will be described hereinafter.

Preparation Series I

Reaction scheme [I]:

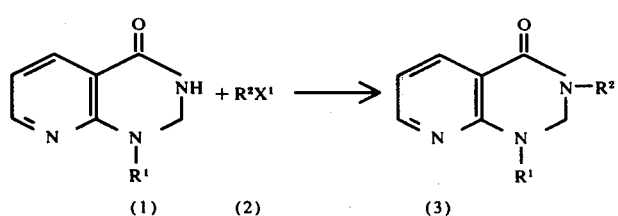

wherein $R^1$ is selected from the group consisting of phenyl and substituted phenyl; $R^2$ is selected from the group consisting of lower alkyl, unsaturated lower alkyl, substituted lower alkyl, lower alkoxycarbonyl and aralkyl; $X^1$ is selected from the gruop consisting of halogen, organic sulfonyloxy, organic sulfonic acid ester rest and inorganic acid ester rest.

Examples of compounds of the general formula (2) include ethyl iodide, propargyl bromide, 2,2,2-trifluoroethyl p-toluenesulfonate, methyl fluorosulfate, dimethyl sulfate, dimethyl sulfite and trimethyl phosphate.

Reaction scheme [II]:

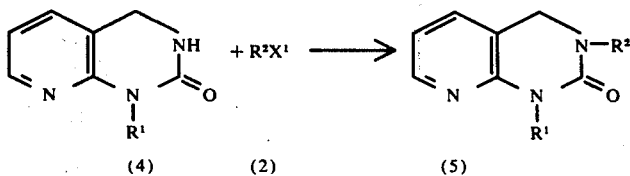

wherein $R^1$, $R^2$ and $X^1$ have the same meanings as defined above.

Reaction scheme [III]:

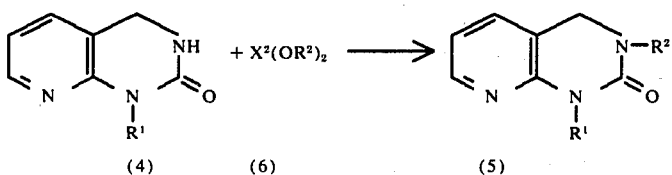

wherein $R^1$ and $R^2$ have the same meanings as defined above; $X^2$ is selected from the group consisting of carbonyl, oxalyl, malonyl, succinyl, maleoyl and fumaroyl. Examples of compounds of the general formula (6) include diethyl carbonate, diethyl oxalate, diethyl malonate, dimethyl succinate, diethyl maleate and diethyl fumarate.

Reaction scheme [IV]:

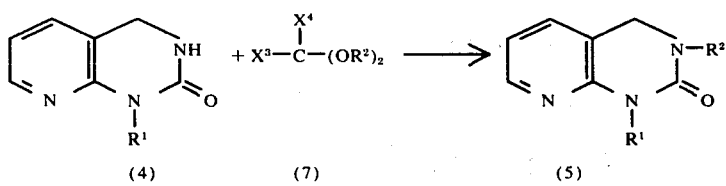

wherein $R^1$ and $R^2$ have the same meanings as defined above; $X^3$ is selected from the group consisting of di(-lower alkyl)amino and lower alkoxy; $X^4$ is selected from the group consisting of hydrogen and lower alkyl. Examples of compounds of the general formula (7) include N,N-dimethylformamide dimethylacetal, N,N-dimethylformamide diisopropylacetal, N,N-dimethylformamide ethyleneacetal and ethyl orthoformate.

The starting materials represented by the general formulas (1) and (4) may be reacted with the said reagents of the general formulas (2), (6) and (7).

These reactions are preferably carried out in an organic solvent such as toluene, xylene, benzene, tetrahydrofuran, dioxane, dimethylformamide, diglyme, chloroform or alcohol.

The reactions illustrated by the schemes [I], [II] and [III] should preferably be processed in the presence of a metallic compound such as potassium amide, sodium amide, sodium hydride or sodium ethylate, an organic base such as pyridine or trialkylamine, or an inorganic base such as alkali hydroxide or alkali carbonate. The first-mentioned metallic compounds are the most effective to obtain the highest yield of the object compounds. The desirable temperature is not critical, and may be ambient or elevated temperature.

In the reaction scheme [IV], the reactions may be carried out in the presence of an organic solvent such as chloroform, benzene, toluene and xylene either at a temperature of 60° – 200° C in a sealed-tube or under reflux.

Preparation series II

Reaction scheme [V]:

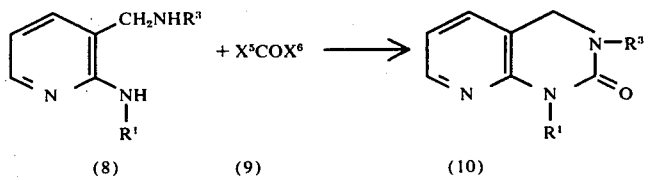

wherein $R^1$ has the same meanings as defined above; $R^3$ is selected from the group consisting of hydrogen, lower alkyl, unsaturated lower alkyl, substituted lower alkyl, lower alkoxycarbonyl and aralkyl; $X^5$ is selected from the group consisting of halogen, lower alkoxy, amino and imidazolyl; $X^6$ is selected from the group consisting of halogen, trihaloalkyl, lower alkoxy, amino and imidazolyl. Examples of compounds of the general formula (9) include urea, methylurea, diethylurea, N,N'-carbonyldiimidazole, phosgene, ethyl chlorocarbonate and diethyl carbonate.

The reactions illustrated by the scheme [V] are generally carried out in an inert solvent such as diglyme, tetrahydrofuran, dioxane, benzene, toluene, xylene, dimethylformamide or alcohol. In the preferred procedure, the reactions are carried out in the presence of a metallic compound such as sodium amide, sodium hydride or sodium ethylate, an organic base such as pyridine or trialkylamine, or an inorganic base such as alkali hydroxide or alkali carbonate. The employment of the first-mentioned metallic compounds are advantageous in producing the highest yield of the desired compounds. The reactions proceed even in the absence of a catalyst when $R^3$ in the general formula (8) is hydrogen or when N,N'-carbonyldiimidazole is used as the reactant (9). The reaction temperature is not critical, but a considerable reduction in time can be brought about when the reactions are performed at or near the boiling point of the solvent used.

Preparation series III

Reaction scheme [VI]

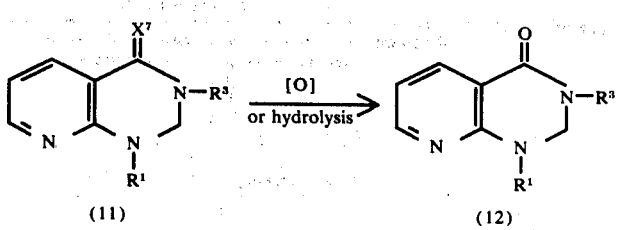

wherein R¹ and R³ have the same meanings as defined above; X⁷ is selected from the group consisting of sulfur and imino. Examples of the oxidizing agents include hydrogen peroxide, permanganate, chromate and dichromate.

The reactions illustrated by the scheme [VI] are generally carried out in a suitable solvent such as water, alcohol, dioxane, tetrahydrofuran, acetone or dimethylsulfoxide in the presence of an acid such as hydrochloric acid, sulfuric acid or phosphoric acid, or a base such as alkali hydroxides, alkali carbonates, alkali earth hydroxides, or ammonium hydroxide. The aforesaid reactions proceed even at room temperature, but the reaction time can be shortened by application of heat.

Preparation series IV

Reaction scheme [VII]

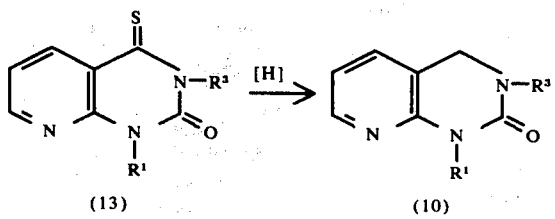

wherein R¹ and R³ have the same meanings as defined above.

Reaction scheme [VIII]

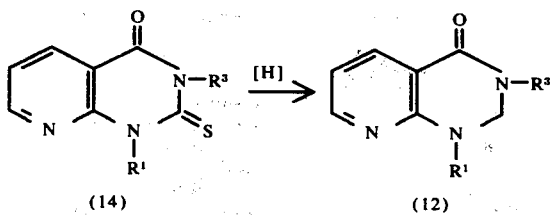

wherein R¹ and R³ have the same meanings as defined above. The reactions illustrated by the schemes [VII] and [VIII] are generally carried out in an organic solvent such as tetrahydrofuran, alcohol or acetone with active Raney nickel by heating.

In the reaction schemes [I] – [VIII], the reaction mixture is concentrated under reduced pressure and the residue obtained is purified either by recrystallization from an organic solvent such as ether, petroleum ether, chloroform and methanol or by column chromatography to give pure crystals of the desired compounds.

The preparations of the starting materials represented by the general formulas (1), (4), (8), (11), (13) and (14) are illustrated hereinafter. The compounds of the general formula (1) may be prepared by reducing 4-oxo-1,4-dihydropyrido[2,3-d]pyrimidine derivatives with sodium borohydride. The compounds of the general formula (4) may be prepared by reacting 2-anilino-3-hydroxymethylpyridine derivatives with urea. The compounds of the general formula (8) may be prepared by reacting 2-anilino-3-halomethylpyridine derivatives with amines. The compounds of the general formula (11) may be prepared by reacting 4-oxo-1,2,3,4-tetrahydropyrido[2,3-d]pyrimidine derivatives with either phosphorus pentasulfide or amines and phosphorus trichloride. The compounds of the general formula (13) may be prepared by reacting pyrido[2,3-d]pyrimidine-2,4(1H,3H)-dione derivatives with phosphorus pentasulfide. The compounds of the general formula (14) may be prepared by reacting 2-anilinonicotinamide derivatives with thiophosgene. These preparations are not to be construed as limiting the preparations of the aforesaid starting materials.

The obtained compounds may be further led to the formation of addition salts with a variety of inorganic and organic acids. Some typical examples of these salts include hydrochloride, sulfate, phosphate, acetate, benzoate, lactate, succinate, citrate, tartrate, fumarate, malonate and maleate. These salts are embraced within the scope of the present invention, of course, and this formation of salts serves to improve the solubility and stability of the object compounds.

Compound

The object compounds of the present invention can be prepared by the processes described in Preparation series I–IV. Examples of the compounds and the melting points thereof are shown in Table I.

Table I- (1)

Examples of the compounds of the general formula (I) obtained by the present invention

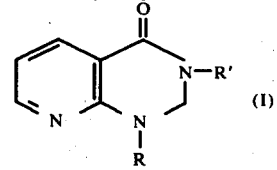

| Compound No. | R | R' | Melting point (° C) |
|---|---|---|---|
| 1 | ⟨phenyl⟩ | —H | 209–211 |
| 2 | " | —CH₃ | 140–141 |
| 3 | " | —C₂H₅ | 211–212 |
| 4 | " | —CH(CH₃)₂ | 123–124 |
| 5 | " | —CH₂CH=CH₂ | 88–89 |
| 6 | " | —CH₂-⟨cyclopropyl⟩ | 93–94 |
| 7 | " | —CH₂CF₃ | 149–151 |
| 8 | " | —CH₂OCH₃ | 104–106 |

Table I-(1)-continued

Examples of the compounds of the general formula (I) obtained by the present invention

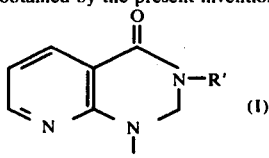

(I)

| Compound No. | R | R' | Melting point (°C) |
|---|---|---|---|
| 9 | 2-F-phenyl | —H | 213-214 |
| 10 | 3-F-phenyl | —H | 201-202 |
| 11 | " | —C₂H₅ | 123-124 |
| 12 | " | —CH(CH₃)₂ | 108-109 |
| 13 | " | —CH₂-cyclopropyl | 69-70 |
| 14 | 3-F-phenyl | —CH₂CF₃ | 168-169 |
| 15 | " | —CH₂OCH₃ | 57-58 |
| 16 | 4-F-phenyl | —H | 239-242 |
| 17 | " | —CH(CH₃)₂ | 142-144 |
| 18 | " | —CH₂-cyclopropyl | 105-107 |
| 19 | " | —CH₂OCH₃ | 73-74 |
| 20 | 3-Cl-phenyl | —H | 183-184 |
| 21 | " | —CH₃ | 155-156 |
| 22 | " | —C₂H₅ | 95-96 |
| 23 | " | —CH₂CH₂CH₃ | oil |
| 24 | " | —CH(CH₃)₂ | 89-90 |
| 25 | " | —CH₂C≡CH | 108-109 |
| 26 | " | —CH₂-cyclopropyl | oil |
| 27 | " | —CH₂CF₃ | 108-109 |
| 28 | " | —CH₂OCH₃ | oil |
| 29 | 4-Cl-phenyl | —H | 208-209 |
| 30 | " | —CH₃ | 181-182 |
| 31 | " | —C₂H₅ | 100-101 |
| 32 | 4-Cl-phenyl | —CH(CH₃)₂ | 133-134 |
| 33 | " | —CH₂-cyclopropyl | oil |
| 34 | " | —CH₂CH₂OH | 140-141 |
| 35 | 3-Br-phenyl | —H | 188-189 |
| 36 | " | —CH₃ | 162-163 |
| 37 | " | —C₂H₅ | 120-121 |
| 38 | " | —CH(CH₃)₂ | 109-110 |
| 39 | " | —CH₂CH=CH₂ | oil |
| 40 | " | —CH₂C≡CH | 120-121 |

Table I-(1)-continued

Examples of the compounds of the general formula (I) obtained by the present invention

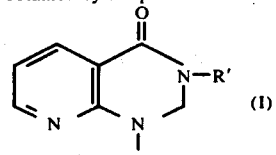

(I)

| Compound No. | R | R' | Melting point (°C) |
|---|---|---|---|
| 41 | " | —CH₂-cyclopropyl | oil |
| 42 | " | —CH₂CF₃ | 136-137 |
| 43 | " | —CH₂CH₂Cl | 115-116 |
| 44 | " | —CH₂CH₂OH | 110-111 |
| 45 | " | —CH₂OCH₃ | 79-80 |
| 46 | 3-I-phenyl | —H | 205-206 |
| 47 | " | —CH(CH₃)₂ | 124-125 |
| 48 | " | —CH₂-cyclopropyl | 78-80 |
| 49 | " | —CH₂OCH₃ | 73-74 |
| 50 | 3-CF₃-phenyl | —H | 166-167 |
| 51 | " | —CH₃ | 139-141 |
| 52 | " | —C₂H₅ | 108-109 |
| 53 | " | —CH₂CH₂CH₃ | 57-59 |
| 54 | " | —CH(CH₃)₂ | oil |
| 55 | " | —CH₂CH=CH₂ | 65-66 |
| 56 | " | —CH₂C≡CH | 114-115 |
| 57 | " | —CH₂-cyclopropyl | 78-80 |
| 58 | " | —CH₂CF₃ | 97-99 |
| 59 | " | —CH₂CH₂Cl | 121-122 |
| 60 | " | —CH₂CH₂OH | 109-111 |
| 61 | " | —CH₂OCH₃ | oil |
| 62 | " | —CH₂CH₂OCO-CH₃ | 94-95 |
| 63 | 3-NO₂-phenyl | —H | 245-247 |
| 64 | " | —CH₃ | 247-248 |
| 65 | " | —C₂H₅ | 124-125 |
| 66 | " | —CH(CH₃)₂ | 136-138 |
| 67 | " | —CH₂C≡CH | 123-124 |
| 68 | 3-NO₂-phenyl | —CH₂-cyclopropyl | 119-120 |
| 69 | " | —CH₂CF₃ | 145-146 |
| 70 | " | —CH₂OCH₃ | 97-98 |
| 71 | " | —CH₂OCH₃ | 137-140 (Hydrochloride) |
| 72 | 3-CH₃-phenyl | —H | 215-217 |
| 73 | " | —C₂H₅ | 112-114 |
| 74 | " | —CH₂CH=CH₂ | oil |
| 75 | " | —CH₂C≡CH | 103-104 |
| 76 | 2,4-Cl₂-phenyl | —H | 229-230 |
| 77 | " | —CH₃ | 181-182 |
| 78 | " | —C₂H₅ | 139-140 |

Table I-(1)-continued

Examples of the compounds of the general formula (I) obtained by the present invention

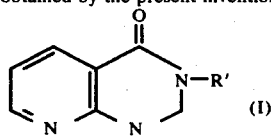

| Compound No. | R | R' | Melting point (° C) |
|---|---|---|---|
| 79 | " | —CH(CH₃)₂ | 102–103 |
| 80 | " | —CH₂-cyclopropyl | 118–120 |
| 81 | " | —CH₂CF₃ | 94–95 |
| 82 | " | —CH₂CH₂Cl | 117–118 |
| 83 | " | —CH₂CH₂OH | 137–138 |
| 84 | " | —CH₂OCH₃ | 95–97 |
| 85 | 2-CH₃,3-Cl-phenyl | —H | 210–211 |
| 86 | 2-CH₃,3-Cl-phenyl | —C₂H₅ | 161–163 |
| 87 | 2,6-(CH₃)₂-phenyl | —H | 269–270 |
| 88 | " | —CH₃ | 165–167 |
| 89 | " | —CH₂CH₂OC₂H₅ | 84–85 |

Table I-(2)

Examples of the compounds of the general formula (II) obtained by the present invention

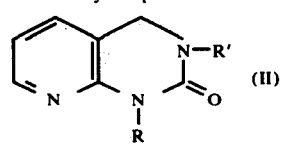

| Compound No. | R | R' | Melting point (° C) |
|---|---|---|---|
| 1 | phenyl | —H | 258–260 |
| 2 | " | —CH₃ | 194–196 |
| 3 | " | —C₂H₅ | 176–177 |
| 4 | " | —CH₂CH₂CH₃ | 129–130 |
| 5 | " | —CH(CH₃)₂ | 164–165 |
| 6 | " | —CH₂CH=CH₂ | 143–144 |
| 7 | " | —CH₂CH=C(CH₃)₂ | 149–150 |
| 8 | " | —CH₂C≡CH | 164–165 |
| 9 | " | —CH₂-cyclopropyl | 120–121 |
| 10 | " | —CH₂-phenyl | 134–135 |
| 11 | 2-F-phenyl | —H | 213–214 |
| 12 | " | —CH₃ | 143–144 |
| 13 | " | —C₂H₅ | 95–97 |

Table I-(2)-continued

Examples of the compounds of the general formula (II) obtained by the present invention

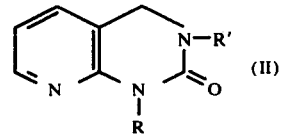

| Compound No. | R | R' | Melting point (° C) |
|---|---|---|---|
| 14 | 2-F-phenyl | —CH(CH₃)₂ | 120–121 |
| 15 | " | —CH₂CH=CH₂ | 129–130 |
| 16 | " | —CH₂C≡CH | 137–138 |
| 17 | 3-F-phenyl | —H | 250–252 |
| 18 | " | —CH₃ | 189–192 |
| 19 | " | —C₂H₅ | 175–176 |
| 20 | " | —CH₂CH₂CH₃ | 121–123 |
| 21 | " | —CH(CH₃)₂ | 146–148 |
| 22 | " | —CH₂CH=CH₂ | 127–128 |
| 23 | " | —CH₂C≡CH | 160–163 |
| 24 | " | —CH₂-cyclopropyl | 96–98 |
| 25 | " | —CH₂CH₂OC₂H₅ | 123–124 |
| 26 | " | —COOC₂H₅ | 152–154 |
| 27 | 4-F-phenyl | —H | 266–267 |
| 28 | " | —CH₃ | 212–213 |
| 29 | " | —C₂H₅ | 192–193 |
| 30 | " | —CH₂CH₂CH₃ | 146–148 |
| 31 | " | —CH(CH₃)₂ | 190–191 |
| 32 | " | —CH₂CH=CH₂ | 118–120 |
| 33 | " | —CH₂-cyclopropyl | 136–138 |
| 34 | " | —CH₂CH₂OC₂H₅ | 119–121 |
| 35 | 2-Cl-phenyl | —H | 239–241 |
| 36 | " | —CH₃ | 169–173 |
| 37 | " | —C₂H₅ | 125–128 |
| 38 | " | —CH₂CH₂CH₃ | 101–103 |
| 39 | " | —CH(CH₃)₂ | 156–159 |
| 40 | " | —CH₂CH=CH₂ | 101–103 |
| 41 | " | —CH₂C≡CH | 127–129 |
| 42 | " | —CH₂-cyclopropyl | 136–139 |
| 43 | " | —CH₂CH₂F | 107–110 |
| 44 | " | —CH₂CH₂OH | 106–107 |
| 45 | " | —CH₂CH₂N(CH₃)₂ | 239–241 (Hydrochloride) |
| 46 | 3-Cl-phenyl | —H | 208–210 |
| 47 | " | —CH₃ | 140–141 |
| 48 | " | —C₂H₅ | 125–126 |
| 49 | " | —CH₂CH₂CH₃ | 95–98 |
| 50 | 4-Cl-phenyl | —CH(CH₃)₂ | 81–82 |
| 51 | " | —CH₂CH=CH₂ | 112–114 |

Table I-(2)-continued

Examples of the compounds of the general formula (II) obtained by the present invention

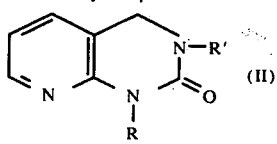

(II)

| Compound No. | R | R' | Melting point (°C) |
|---|---|---|---|
| 52 | " | —CH$_2$C≡CH | 111–112 |
| 53 | " | —CH$_2$-cyclopropyl | 120–121 |
| 54 | " | —CH$_2$CH$_2$OC$_2$H$_5$ | 100–101 |
| 55 | " | —CH$_2$OCH$_3$ | 128–129 |
| 56 | 4-Cl-phenyl | —H | 289–291 |
| 57 | " | —CH$_3$ | 170–171 |
| 58 | " | —C$_2$H$_5$ | 173–174 |
| 59 | " | —CH$_2$CH$_2$CH$_3$ | 129–131 |
| 60 | " | —CH(CH$_3$)$_2$ | 170–173 |
| 61 | " | —CH$_2$CH=CH$_2$ | 159–161 |
| 62 | " | —CH$_2$C≡CH | 167–168 |
| 63 | " | —CH$_2$-cyclopropyl | 148–150 |
| 64 | 3-Br-phenyl | —H | 210–211 |
| 65 | " | —CH$_3$ | 130–132 |
| 66 | " | —C$_2$H$_5$ | 103–105 |
| 67 | " | —CH$_2$CH$_2$CH$_3$ | 108–109 |
| 68 | " | —CH(CH$_3$)$_2$ | 119–122 |
| 69 | " | —CH$_2$CH=CH$_2$ | 117–119 |
| 70 | " | —CH$_2$C≡CH | 118–119 |
| 71 | " | —CH$_2$-cyclopropyl | 134–135 |
| 72 | " | —CH$_2$CH$_2$OH | 121–123 |
| 73 | " | —CH$_2$CH$_2$OC$_2$H$_5$ | 104–105 |
| 74 | " | —CH$_2$CH$_2$OCOCH$_3$ | 99–100 |
| 75 | 3-I-phenyl | —H | 175–177 |
| 76 | " | —C$_2$H$_5$ | 137–139 |
| 77 | 3-CF$_3$-phenyl | —H | 216–217 |
| 78 | " | —CH$_3$ | 122–123 |
| 79 | " | —C$_2$H$_5$ | 155–157 |
| 80 | " | —CH$_2$CH$_2$CH$_3$ | 99–101 |
| 81 | " | —CH(CH$_3$)$_2$ | 167–168 |
| 82 | " | —CH$_2$CH=CH$_2$ | 107–109 |
| 83 | " | —CH$_2$CH=C(CH$_3$)$_2$ | 80–81 |
| 84 | " | —CH$_2$C≡CH | 111–112 |
| 85 | " | —CH$_2$-cyclopropyl | 121–122 |
| 86 | 3-CF$_3$-phenyl | —CH$_2$CF$_3$ | 131–132 |
| 87 | " | —CH$_2$CH$_2$OH | 120–121 |
| 88 | " | —CH$_2$CH$_2$CH$_2$OH | 107–109 |
| 89 | " | —CH$_2$CH$_2$OC$_2$H$_5$ | 98–99 |
| 90 | " | —CH$_2$OCH$_3$ | 129–130 |
| 91 | " | —CH$_2$CH$_2$OCOCH$_3$ | 105–106 |

Table I-(2)-continued

Examples of the compounds of the general formula (II) obtained by the present invention

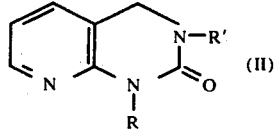

(II)

| Compound No. | R | R' | Melting point (°C) |
|---|---|---|---|
| 92 | " | —CH$_2$COOH | 223–225 |
| 93 | " | —COOCH$_3$ | 120–122 |
| 94 | " | —COOC$_2$H$_5$ | 113–114 |
| 95 | " | —CH$_2$-phenyl | 112–113 |
| 96 | " | —CH$_2$CH$_2$CH$_2$N(CH$_3$)$_2$ | 256–257 (Hydrochloride) |
| 97 | 3-NO$_2$-phenyl | —H | 134–136 |
| 98 | " | —CH$_3$ | 179–182 |
| 99 | " | —C$_2$H$_5$ | 155–156 |
| 100 | " | —CH$_2$CH$_2$CH$_3$ | 157–158 |
| 101 | " | —CH(CH$_3$)$_2$ | 188–189 |
| 102 | " | —CH$_2$CH=CH$_2$ | 138–139 |
| 103 | " | —CH$_2$C≡CH | 187–189 |
| 104 | 4-NO$_2$-phenyl | —CH$_2$-cyclopropyl | 167–169 |
| 105 | " | —CH$_2$CH$_2$OC$_2$H$_5$ | 160–162 |
| 106 | " | —CH$_2$-phenyl | 141–143 |
| 107 | 3-CH$_3$-phenyl | —H | 212–214 |
| 108 | " | —C$_2$H$_5$ | 107–110 |
| 109 | " | —CH$_2$C≡CH | 102–105 |
| 110 | " | —CH$_2$-cyclopropyl | 134–136 |
| 111 | 3,4-diCl-phenyl | —H | 262–263 |
| 112 | " | —CH$_3$ | 149–150 |
| 113 | " | —C$_2$H$_5$ | 135–136 |
| 114 | " | —CH$_2$CH$_2$CH$_3$ | 103–105 |
| 115 | " | —CH(CH$_3$)$_2$ | 150–151 |
| 116 | " | —CH$_2$CH=CH$_2$ | 129–131 |
| 117 | " | —CH$_2$C≡CH | 129–130 |
| 118 | " | —CH$_2$-cyclopropyl | 114–116 |
| 119 | " | —CH$_2$CH$_2$F | 122–123 |
| 120 | " | —CH$_2$CH$_2$OH | 141–142 |
| 121 | " | —CH$_2$CH$_2$OC$_2$H$_5$ | 111–113 |
| 122 | 2,3-diCl-phenyl | —CH$_2$CH$_2$OCOCH$_3$ | 102–104 |
| 123 | " | —COOCH$_3$ | 156–160 |
| 124 | " | —CH$_2$-phenyl | 105–107 |

Pharmacological activities

With respect to numerous compounds of the present invention, the acute toxicity was tested to ensure their safety, and further central nervous system depressive, anti-inflammatory and analgetic effects were tested to prove their excellent activities. The results of each test are indicated in Table II. Each test was conducted in the following manner.

1. Acute toxicity

Each test compound suspended in 0.5% tragacanth-saline solution was administered intraperitoneally or orally to dd-strain male mice (16–24 g). The lethal dose was estimated from the death of animals 72 hours after administration.

2. Anti-inflammatory effect

A group of five Wistar-strain male rats (100–150 g) were orally administered with each test compound suspended in 0.5% tragacanth-saline solution. After 30 minutes 0.5–1.0% carrageenin suspended in the water for injection was injected subcutaneously to a hind paw. After 3 hours the carrageenin edema was measured by volume and the inhibition percentage was determined with respect to the results for the control animals. The inhibition percentages were shown with the notations as follows:

less than 15% : ±; 16–30% : +; 31–45% : ++; 46–60% : +++; more than 61% : ++++

3. Analgetic effect

Each test compound suspended in 0.5% tragacanth-saline solution was orally administered to dd-strain male mice (18–20 g). After one hour 0.6% acetic acid solution was intraperitoneally injected in a volume of 0.1 ml/10 g. The writhing syndrome was observed for 10 minutes from 30 minutes after the injection, and 50% analgetic effective dose ($ED_{50}$) and its 95% confidential limits were calculated by Litchfield-Wilcoxon's method.

4. Central nervous system depressive effect

Each test compound suspended in 0.5% tragacanth-saline solution was injected intraperitoneally to dd-strain male mice (16–24 g). The disappearance of righting reflex was observed under noiseless circumstances. The dose required for the disappearance of righting reflex is indicated with the following notations:

| | |
|---|---|
| more than 1,000 (mg/kg) : − | 100–30 (mg/kg) : ++ |
| 1,000–300 (mg/kg) : ± | 30–10 (mg/kg) : +++ |
| 300–100 (mg/kg) : + | 10–3 (mg/kg) : ++++ |
| | less than 3 (mg/kg) : +++++ |

Table II

Anti-inflammatory, Analgetic and Central Nervous System Depressive Effect, and Acute Toxicity of the Object Compounds, Pyrido[2,3-d]pyrimidinones Obtained by the Present Invention:

| Standard compound | anti-inflammatory effect dose(mg/kg) | analgetic effect $ED_{50}$ (95 % C.L.) (mg/kg) | C N S depressive effect | acute toxicity (mg/kg) |
|---|---|---|---|---|
| | 50 | 10 | | i.p. |
| phenylbutazone | ++ | ± 290 (113–435) | ± | 300–1000 |
| flufenamic acid | + | ± 180 (131–245) | − | 300–1000 |
| aminopyrine | ± | ± i.p. 56.0 (43.0–73.0) | / | 100–300 |
| methaqualone | / | / / | +++ | 300–1000 |
| diazepam | + | ± / | ++ | 300–1000 |

Object Compounds of General formula(I)

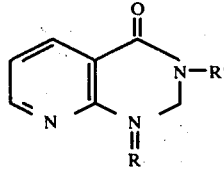

| R | R' | anti-inflammatory effect dose(mg/kg) | analgetic effect $ED_{50}$ (95 % C.L.) (mg/kg) | C N S depressive effect | acute toxicity (mg/kg) | |
|---|---|---|---|---|---|---|
| | | 50 | 10 | | i.p. | p.o. |
| Cl-C₆H₄- | −CH(CH₃)CH₃ | ++ | + | >100 | / | / / |
| " | −CH₂OCH₃ | + | + | > | 100 | / |
| Br-C₆H₄- | −CH₃ | ± | / | >100 | ++ | >1000 / |
| " | −C₂H₅ | ++ | / | >100 | ++ | >1000 / |
| CF₃-C₆H₄- | −CH₃ | ± | + | / | / | / / |
| " | −C₂H₅ | ++++ | + | >100 | ++ | >1000 / |
| NO₂-C₆H₄- | −CH₃ | + | ± | 22.0 (9.0–53.9) | − | >1000 / |

Table II-continued

Anti-inflammatory, Analgetic and Central Nervous System Depressive Effect, and Acute Toxicity of the Object Compounds, Pyrido[2,3-d]pyrimidinones Obtained by the Present Invention:

| R | R' | anti-inflammatory effect | analgetic effect | ED$_{50}$ (95% C.L.) (mg/kg) | CNS depressive effect | acute toxicity (mg/kg) i.p. | acute toxicity (mg/kg) p.o. |
|---|---|---|---|---|---|---|---|
| " | $-C_2H_5$ | ++++ | ++ | 1.95 (0.75–5.05) | ++ | 1000 | 2000 |
| " | $-CH(CH_3)_2$ | +++ | +++ | 4.7 (1.12–19.6) | + | >1000 | <2000 |
| " | $-CH_2OCH_3 \cdot HCl$ | +++ | +++ | 2.7 (0.65–11.3) | / | 100–300 | <2000 |

Object Compounds of General Formula (II)

structure: pyrido[2,3-d]pyrimidinone bearing $-N-R'$, $=N-R$, $=O$ substituents (II)

| R | R' | anti-inflammatory effect dose (mg/kg) 50 | anti-inflammatory effect dose (mg/kg) 10 | analgetic effect ED$_{50}$ (95% C.L.) (mg/kg) | CNS depressive effect | acute toxicity (mg/kg) i.p. | acute toxicity (mg/kg) p.o. |
|---|---|---|---|---|---|---|---|
| phenyl | $-CH_3$ | +++ | ++ | 13.0 (4.68–38.9) | ++++ | 300–1000 | 1000–2000 |
| " | $-C_2H_5$ | +++ | +++ | 2.1 (0.80–5.52) | ++++ | 300 | 500–1000 |
| 3-F-phenyl | $-C_2H_5$ | ++++ | ++++ | 4.4 (1.79–10.8) | +++++ | 300–1000 | 1000–2000 |
| " | $-CH(CH_3)_2$ | ++++ | ++ | 4.5 (1.45–14.0) | ++++ | 300–1000 | / |
| 4-F-phenyl | $-C_2H_5$ | +++ | +++ | 4.9 (1.64–14.6) | +++ | 300–1000 | 500–1000 |
| 2-Cl-phenyl | $-CH_3$ | + | – | 44.0 (14.1–137.7) | ++ | 300–1000 | 1000–2000 |
| 2-Cl-phenyl | $-C_2H_5$ | ++ | / | 26.5 (8.78–80.0) | ++ | 300–1000 | <2000 |
| 3-Cl-phenyl | $-CH_3$ | ++++ | +++ | 13.0 (5.6–30.2) | +++++ | 100–300 | 500–1000 |
| " | $-CH_2CH=CH_2$ | +++ | +++ | 1.2 (0.40–3.59) | ++++ | 300–1000 | 200–500 |
| " | $-CH_2OCH_3$ | ++++ | +++ | 1.6 (0.39–6.53) | ++++ | 100–300 | 200–500 |
| 4-Cl-phenyl | $-C_2H_5$ | +++ | +++ | 49.0 (14.9–161.2) | +++++ | 300–1000 | 1000–2000 |
| 3-Br-phenyl | $-C_2H_5$ | +++ | +++ | 2.85 (1.24–6.53) | +++++ | 100–300 | 500–1000 |
| " | $-CH_2CH_2CH_3$ | +++ | +++ | 2.65 (0.98–7.16) | ++++ | 300–1000 | <2000 |
| 3-CF$_3$-phenyl | $-CH_3$ | +++ | + | 6.6 (2.2–19.8) | ++++ | 300–1000 | <500 |
| " | $-C_2H_5$ | +++ | ++ | 6.3 (2.14–18.5) | ++++ | 300–1000 | 500–1000 |
| " | $-CH(CH_3)_2$ | +++ | ± | 6.7 (2.07–21.7) | +++ | >1000 | 2000 |
| " | $-CH_2CH_2OH$ | + | / | 55.0 (15.7–192.5) | – | >1000 | >2000 |
| " | $-CH_2OCH_3$ | ++ | / | 8.1 (2.36–27.8) | +++ | 300–1000 | 500–1000 |
| " | $-CH_2COOH$ | – | / | >100 | – | >1000 | >2000 |
| 2,3-Cl$_2$-phenyl | $-C_2H_5$ | +++ | +++ | 1.3 (0.51–3.33) | +++++ | 300–1000 | 500–1000 |
| " | $-CH(CH_3)_2$ | ++++ | +++ | 16.3 (9.01–29.5) | ++++ | 1000 | 2000 |
| | | | | 1.0 | | 100– | 200– |

Table II-continued

Anti-inflammatory, Analgetic and Central Nervous System Depressive Effect, and Acute Toxicity of the Object Compounds, Pyrido[2,3-d]pyrimidinones Obtained by the Present Invention:

| " | —$CH_2CH_2F$ | / | ++++ (0.29–3.45) | ++++ | 300 | 500 |

The present invention is further illustrated by the following non-limitive examples.

EXAMPLE 1

To a solution of 2.4 g of 1-(m-fluorophenyl)-4-oxo-1,2,3,4-tetrahydropyrido[2,3-d]pyrimidine and 40 ml of dimethylformamide was added 0.6 g of 50% sodium hydride and the mixture was stirred for one hour at room temperature. To this was further added 4.6 g of ethyl iodide and the resulting mixture was stirred at 60° C for 1.5 hours. After the reaction was finished, the solvent was distilled off from the mixture to leave a residue, to which was added water to precipitate a crude product. Recrystallization of this product from ether gave 2.2 g of 1-(m-fluorophenyl)-3-ethyl-4-oxo-1,2,3,4-tetrahydropyrido[2,3-d]pyrimidine as pale yellow prisms, melting at 123° – 124° C.

Analysis-Calculated for $C_{15}H_{14}ON_3F$: C, 66.41; H, 5.20; N, 15.49. Found: C, 66.62; H, 5.43; N, 15.51.

EXAMPLE 2

To a solution of 2.7 g of 1-(m-nitrophenyl)-4-oxo-1,2,3,4-tetrahydropyrido[2,3-d]pyrimidine and 20 ml of dry dimethylformamide was added 0.48 g of approximately 55% sodium hydride and the mixture was stirred at room temperature for 30 minutes. To this was added dropwise 2.52 g of dimethyl sulfate and the whole was stirred at room temperature for 3 hours. The reaction mixture was neutralized with sodium carbonate and concentrated under reduced pressure to leave a residue, to which was added water to precipitate a crude product. This product was collected by filtration and recrystallized from a mixture of dimethylformamide and methanol to give 1.96 g of 1-(m-nitrophenyl)-3-methyl-4-oxo-1,2,3,4-tetrahydropyrido[2,3-d]pyrimidine as yellow needles, melting at 247° – 248° C.

Analysis-Calculated for $C_{14}H_{12}N_4O_3$: C, 59.15; H, 4.26; N, 19.71. Found: C, 59.01; H, 4.12; N, 19.82.

EXAMPLE 3

To a solution of 3.0 g of 1-(m-bromophenyl)-2-oxo-1,2,3,4-tetrahydropyrido[2,3-d]pyrimidine and 100 ml of dry dimethylformamide was added 0.6 g of 50% sodium hydride and the mixture was stirred for 30 minutes. To this was further added 3.5 g of propargyl bromide and the whole was reacted for one hour at room temperature. After the reaction was complete, the solvent was distilled off from the reaction mixture under reduced pressure. The residue thus obtained was diluted with water to release an oily product, which was then extracted with ether. The ether solution was dehydrated over magnesium sulfate, and separation and purification were accomplished by passing the solution through a column of alumina. The eluate thus obtained was concentrated to give 2.9 g of 1-(m-bromophenyl)-3-propargyl-2-oxo-1,2,3,4-tetrahydropyrido[2,3-d]pyrimidine as colorless prisms, melting at 118° – 119° C.

Analysis-Calculated for $C_{16}H_{12}ON_3Br$: C, 56.16; H, 3.54; N, 12.28. Found: C, 56.01; H, 3.49; N, 12.24.

EXAMPLE 4

To a solution of 3.3 g of 2-(m-iodoanilino)-3-aminomethylpyridine and 30 ml of dry tetrahydrofuran was added 3.2 g of N,N'-carbonyldiimidazole and the mixture was heated under reflux for 12 hours. After the reaction was complete, the solvent was removed from the reaction mixture by distillation under reduced pressure. The residue thus obtained was dissolved in acetone. The acetone solution was placed on a column of alumina and eluted with acetone. The eluate was concentrated and left to yield 2.5 g of 1-(m-iodophenyl)-2-oxo-1,2,3,4-tetrahydropyrido[2,3-d]pyrimidine as colorless needles, melting at 175° – 177° C.

Analysis-Calculated for $C_{13}H_{10}IN_3O$: C, 44.46; H, 2.87; N, 11.97. Found: C, 44.32; H, 2.78; N, 11.88.

EXAMPLE 5

To a solution of 0.7 g of 1-(m-trifluoromethylphenyl)-2-oxo-1,2,3,4-tetrahydropyrido[2,3-d]pyrimidine and 10 ml of dimethylformamide was added 0.13 g of sodium hydride. To this was added a mixture of 5.1 g of methyl iodide and 5 ml of dimethylformamide, dropwise under cooling, and immediately the resulting mixture was heated for 1.5 hour in an oil bath maintained at 100° C. After the reaction was complete, the solvent was distilled off under reduced pressure to leave a residue, to which was added ice-cold water. This residue was extracted with ether, washed and dehydrated. Separation and purification were accomplished by passing the solution through a column of alumina, and the eluate obtained was concentrated to give 0.6 g of 1-(m-trifluoromethylphenyl)-3-methyl-2-oxo-1,2,3,4-tetrahydropyrido[2,3-d]pyrimidine as colorless prisms, melting at 122° – 124° C.

Analysis-Calculated for $C_{15}H_{12}F_3N_3O$: C, 58.63; H, 3.94; N, 13.68. Found: C, 58.52; H, 3.98; N, 13.61.

EXAMPLE 6

To a solution of 2.3 g of 2-(m-fluoroanilino)-3-methylaminomethylpyridine was added 0.96 g of approximately 50% sodium hydride and the mixture was stirred at room temperature for 30 minutes. To this was added 10 g of approximately 30% carbon tetrachloride-phosgene solution, dropwise under ice-cooling, and the resulting mixture was stirred for 1 hour. After an excess of the phosgene was decomposed with 10% acetone-ammonia solution, the solvent was removed from the reaction mixture by distillation under reduced pressure. The residue thus obtained was diluted with water, extracted with ether and dehydrated. The ether solution was applied on a column of alumina and then eluted with ether. The eluate was concentrated and left to give 1.3 g of 1-(m-fluorophenyl)-3-methyl-2-oxo-1,2,3,4-tetrahydropyrido[2,3-d]pyrimidine as colorless prisms, melting at 189° – 192° C.

Analysis-Calculated for $C_{14}H_{12}FN_3O$: C, 65.36; H, 4.70; N, 16.33. Found: C, 63.44; H, 4.72; N, 16.39.

EXAMPLE 7

To a solution of 4.5 g of 1-phenyl-2-oxo-1,2,3,4-tetrahydropyrido[2,3-d]pyrimidine and 50 ml of dry dimethylformamide was added 1.2 g of 50% sodium hydride and the mixture was stirred for 30 minutes at room temperature, and then heated to a temperature of 90° – 100° C. To this was gradually added 1.28 g of isopropyl p-toluenesulfonate and the whole was reacted for 1 hour. After the reaction was complete, the solvent was distilled off from the mixture under reduced pressure. The residue obtained was diluted with water to produce a crude precipitate, which was collected by filtration and then dissolved in ethyl ether. Separation and purification were accomplished by applying the solution on a column of alumina, and the eluate was concentrated to give 4.1 g of 1-phenyl-3-isopropyl-2-oxo-1,2,3,4-tetrahydropyrido[2,3-d]pyrimidine as colorless prisms, melting at 164° – 165° C.

Analysis-Calculated for $C_{16}H_{17}N_3O$: C, 71.88; H, 6.41; N, 15.72. Found: C, 71.75; H, 6.41; N, 15.72.

EXAMPLE 8

To a mixture of 2.0 g of 2-(m-trifluoromethylanilino)-3-ethylaminomethylpyridine, 1.0 g of sodium ethoxide and 30 ml of dioxane was added dropwise 2.4 g of diethyl carbonate, and the mixture was heated under reflux for 5 hours. After the reaction was complete, the dioxane was removed from the reaction mixture by distillation under reduced pressure. The residue thus obtained was recrystallized from ether to yield 2.1 g of 1-(m-trifluoromethylphenyl)-3-ethyl-2-oxo-1,2,3,4-tetrahydropyrido[2,3-d]pyrimidine as colorless prisms, melting at 155° – 157° C.

Analysis-Calculated for $C_{16}H_{14}F_3N_3O$: C, 59.81; H, 4.39; N, 13.07. Found: C, 59.72; H, 4.29; N, 13.11.

EXAMPLE 9

A mixture of 0.5 g 1-(m-trifluoromethylphenyl)-2-oxo-1,2,3,4-tetrahydropyrido[2,3-d]pyrimidine, 0.8 g of dimethylcarbonate and 10 ml of dimethylformamide was reacted at 160° – 170° C in sealed-tube for 20 hours. After the reaction was finished, the solvent was distilled off from the mixture to leave a residue, to which was added water. This residue was extracted with ether and then dehydrated. The ether solution was applied on a column of alumina, and then eluted with ether. The ether was evaporated from the eluate and left to give 0.4 g of 1-(m-trifluoromethylphenyl)-3-methyl-2-oxo-1,2,3,4-tetrahydropyrido[2,3-d]pyrimidine as colorless prisms, melting at 122° – 124° C.

Analysis-Calculated for $C_{15}H_{12}F_3N_3O$: C, 58.63; H, 3.93; N, 13.67.; Found: C, 58.52; H, 3.89; N, 13.62.

EXAMPLE 10

To a solution of 2.4 g of 1-(p-fluorophenyl)-2-oxo-1,2,3,4-tetrahydropyrido[2,3-d]pyrimidine and 15 ml of dimethylformamide was added 0.5 g of approximately 50% sodium hydride, and the mixture was allowed to stand until the evolution of hydrogen ceased. To this was further added 5.9 g of dimethyl oxalate and the resulting mixture was heated at 170° C in a sealed-tube for 12 hours. After the reaction was complete, the solvent was removed from the reaction mixture by distillation under reduced pressure. The residue thus obtained was diluted with water, extracted with ether and dehydrated. The ether solution was concentrated and left to give 1.6 g of 1-(p-fluorophenyl)-3-methyl-2-oxo-1,2,3,4-tetrahydropyrido[2,3-d]pyrimidine as colorless needles, melting at 212° – 213° C.

Analysis-Calculated for $C_{14}H_{12}FN_3O$: C, 65.36; H, 4.70; N, 16.33. Found: C, 65.21; H, 4.59; N, 16.24.

EXAMPLE 11

To a solution of 2.6 g of 1-(m-chlorophenyl)-2-oxo-1,2,3,4-tetrahydropyrido[2,3-d]pyrimidine and 20 ml of dimethylformamide was added 0.6 g of sodium hydride and the mixture was stirred for 15 minutes. To this was further added 3.4 g of fluoromethylsulfate, and stirring was continued for 1.5 hours at room temperature. After the reaction was finished, the solvent was distilled off from the resulting mixture under reduced pressure. The residue thus obtained was diluted with water, extracted with ether and dehydrated. The ether solution was applied on a column of alumina, and then eluted with ether. The ether was evaporated from the eluate, and the residue was recrystallized from a mixture of ether and petroleum ether to give 2.1 g of 1-(m-chlorophenyl)-3-methyl-2-oxo-1,2,3,4-tetrahydropyrido[2,3-d]pyrimidine as colorless prisms, melting at 139° – 140° C.

Analysis-Calculated for $C_{14}H_{12}ClN_3O$: C, 56.95; H, 4.10; N, 14.23. Found: C, 56.89; H, 4.12; N, 14.25.

EXAMPLE 12

To a solution of 2.2 g of 1-phenyl-2-oxo-1,2,3,4-tetrahydropyrido[2,3-d]pyrimidine and 20 ml of dimethylformamide was added 0.5 g of approximately 50% sodium hydride, and the mixture was allowed to stand at room temperature for 30 minutes. To this was further added dropwise 4.2 g of trimethyl phosphate and the resulting mixture was heated at a temperature of 170° – 180° C in a sealed-tube for 7 hours. After the reaction was complete, the solvent was removed from the reaction mixture by distillation under reduced pressure. The residue thus obtained was diluted with water, extracted with ether and dehydrated. The ether was removed by evaporation to leave a residue. This residue was recrystallized from a mixture of ether and petroleum ether to yield 1.7 g of 1-phenyl-3-methyl-2-oxo-1,2,3,4-tetrahydropyrido[2,3-d]pyrimidine as colorless prisms, melting at 172° – 173° C.

Analysis-Calculated for $C_{14}H_{13}N_3O$: C, 70.27; H, 5.48; N, 17.56. Found: C, 70.11; H, 5.38; N, 17.42.

EXAMPLE 13

To a mixture of 2.9 g of 1-(m-trifluoromethylphenyl)-2-oxo-1,2,3,4-tetrahydropyrido[2,3-d]pyrimidine, 25 ml of dimethylformamide and 4.4 g of dimethylformamide diethylacetal was reacted at 145° – 150° C for 5 hours. After the reaction was complete, the solvent was distilled off from the mixture under reduced pressure. The residue thus obtained was diluted with water, extracted with ether and dehydrated. The ether solution was applied on a column of alumina and then eluted with ether. The eluate was concentrated by evaporation to leave a residue, which was then recrystallized from a mixture of ether and petroleum ether to give 0.6 g of 1-(m-trifluoromethylphenyl)-3-ethyl-2-oxo-1,2,3,4-tetrahydropyrido[2,3-d]pyrimidine as colorless prisms, melting at 155° – 157° C.

EXAMPLE 14

To a mixture of 4.3 g 2-(m-toluidino)-3-aminomethylpyridine and 12 g of urea was heated at 180° C for 2 hours and further heated at 200° C for 30 minutes.

After cooling, crude reaction product precipitated was collected by filtration and washed with sufficient amounts of warm water. This product was purified by recrystallization from methanol to give 2.6 g of 1-(m-tolyl)-2-oxo-1,2,3,4-tetrahydropyrido[2,3-d]pyrimidine as colorless prisms, melting at 212° – 214° C.

Analysis-Calculated for $C_{14}H_{11}N_3O$: C, 70.87; H, 4.76; N, 17.71. Found: C, 70.63; H, 4.59; N, 17.66.

EXAMPLE 15

A mixture of 2.5 g of 1-phenyl 3-methyl-4-thio-1,2,3,4-tetrahydropyrido[2,3-d]pyrimidine, 20 ml of tetrahydrofuran and 20 ml of 30% hydrogen peroxide was refluxed for 2 hours. After the reaction was finished, the reaction solvent was distilled off from the mixture under reduced pressure. The residue thus obtained was recrystallized from ether to yield 2.1 g of 1-phenyl-3-methyl-4-oxo-1,2,3,4-tetrahydropyrido[2,3-d]pyrimidine as colorless prisms, melting at 140° – 141° C.

Analysis-Calculated for $C_{14}H_{13}N_3O$: C, 70.27; H, 5.48; N, 17.56. Found: C, 70.12; H, 5.42; N, 17.54.

EXAMPLE 16

A mixture of 3.4 g of 1-(m-trifluoromethylphenyl)-3-ethylimino-pyrido-1,2,3,4-tetrahydropyrido[2,3-d] pyrimidine, 40 ml of 15% hydrochloric acid was refluxed for 3 hours. After the reaction was finished, the reaction mixture was neutralized with 5% sodium carbonate solution, and then extracted with ether. The ether solution was concentrated by evaporation and allowed to stand for producing 2.4 g of 1-(m-trifluoromethylphenyl)-3-ethyl-4-oxo-1,2,3,4-tetrahydropyrido[2,3-d]pyrimidine as colorless needles, melting at 108° – 109° C.

Analysis-Calculated for $C_{16}H_{14}F_3N_3O$: C, 59.81; H, 4.39; N, 13.08. Found: C, 59.69; H, 4.36; N, 13.09.

EXAMPLE 17

To a solution of 3 g of 1-(p-chlorophenyl)-3-ethyl-4-thio-1,2,3,4-tetrahydropyrido[2,3-d]pyrimidine and 100 ml of methanol was added 40 ml of 5% sodium hydroxide solution and the mixture was refluxed for 3 hours. Then, the reaction mixture was concentrated to give a residue, to which was added water. A crude product precipitated was collected by filtration and washed and dried. Recrystallization of this product from ethyl ether yielded 2.6 g of 1-(p-chlorophenyl)-3-ethyl-4-oxo-1,2,3,4-tetrahydropyrido[2,3-d]pyrimidine, melting at 100° – 101° C.

Analysis-Calculated for $C_{15}H_{14}ClN_3O$: C, 62.61; H, 4.90; N, 14.60. Found: C, 62.48; H, 4.82; H, 14.53.

EXAMPLE 18

To 100 ml of methanol was added some amounts of activating Raney nickel (prepared by treating 10 g of Al-Ni alloy with NaOH solution) and 2.6 g of 1-phenyl-2-oxo-4-thio--1,2,3,4-tetrahydropyrido[2,3-d]pyrimidine and the mixture was refluxed for 4 hours. After the reaction was finished, the resulting mixture was filtered to remove Raney nickel and then concentrated under reduced pressure to give a residue. This residue was purified by recrystallization from methanol to yield 1.6 g of 1-phenyl-2-oxo-1,2,3,4-tetrahydropyrido[2,3-d]pyrimidine as colorless needles, melting at 269° – 271° C.

Analysis-Calculated for $C_{13}H_{11}N_3O$: C, 69.32; H, 4.92; N, 18.66. Found: C, 69.18; H, 4.82; N, 18.71.

EXAMPLE 19

1.0 g of 1-(m-trifluoromethylphenyl)-3-ethyl-2-thio-4-oxo-1,2,3,4-tetrahydropyrido[2,3-d]pyrimidine was dissolved in 50 ml of ethanol and reduced in the presence of Raney nickel at ordinarly pressure and temperature. After the reaction was complete, the Raney nickel was filtered off and the solvent was distilled off from the reaction mixture under reduced pressure. The residue thus obtained was applied on a column of alumina and then eluted with ether. The eluate was concentrated under reduced pressure to leave a residue. This residue was further purified by recrystallization from isopropylether to give 0.7 g of 1-m-trifluoromethylphenyl)-3-ethyl-4-oxo-1,2,3,4-tetrahydropyrido[2,3-d]pyrimidine as colorless needles, melting at 108° – 109° C.

Analysis-Calculated for $C_{16}H_{14}F_3N_3O$: C, 59.81; H, 4.39; N, 13.07. Found: C, 59.85; H, 4.32; N, 13.13.

What is claimed is:

1. A compound of the formula:

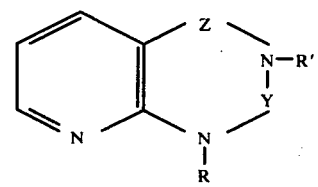

wherein R is selected from the group consisting of phenyl, chlorophenyl, bromophenyl, fluorophenyl, dichlorophenyl, nitrophenyl and trifluoromethylphenyl; R' is selected from the group consisting of methyl, ethyl, propyl, isopropyl, allyl, 2-fluoroethyl, 2-hydroxyethyl, methoxymethyl and carboxymethyl; Y and Z are selected from the group consisting of carbonyl and methylene, but Y and Z are always dissimilar.

2. A compound in accordance with claim 1 of the formula:

wherein R is selected from the group consisting of nitrophenyl and trifluoromethylphenyl; R' is selected from the group consisting of methyl, ethyl, isopropyl and methoxymethyl.

3. A compound in accordance with claim 1 of the formula:

wherein R is selected from the group consisting of phenyl, chlorophenyl, bromophenyl, fluorophenyl, dichlorophenyl and trifluoromethylphenyl; R' is selected from the group consisting of methyl, ethyl, propyl, isopropyl, allyl, 2-fluoroethyl, 2-hydroxyethyl, methoxymethyl and carboxymethyl.

4. A compound in accordance with claim 1 which is: 1-(m-trifluoromethylphenyl)-3-ethyl-4oxo-1,2,3,4-tetrahydropyrido[2,3-d]pyrimidine.

5. A compound in accordance with claim 1 which is: 1-(m-nitrophenyl)-3-ethyl-4-oxo-1,2,3,4-tetrahydropyrido[2,3-d]pyrimidine.

6. A compound in accordance with claim 1 which is: 1-(m-nitrophenyl)-3-isopropyl-4-oxo-1,2,3,4-tetrahydropyrido[2,3-d]pyrimidine.

7. A compound in accordance with claim 1 which is: 1-(m-nitrophenyl)-3-methoxymethyl-4-oxo-1,2,3,4-tetrahydropyrido[2,3-d]-pyrimidine hydrochloride.

8. A compound in accordance with claim 1 which is: 1-phenyl-3-methyl-2-oxo-1,2,3,4-tetrahydropyrido[2,3-d]pyrimidine.

9. A compound in accordance with claim 1 which is: 1-phenyl-3-ethyl-2-oxo-1,2,3,4-tetrahydropyrido[2,3-d]pyrimidine.

10. A compound in accordance with claim 1 which is: 1-(m-fluorophenyl)-3-ethyl-2-oxo-1,2,3,4-tetrahydropyrido[2,3-d]pyrimidine.

11. A compound in accordance with claim 1 which is: 1-(m-fluorophenyl)-3-isopropyl-2-oxo-1,2,3,4-tetrahydropyrido[2,3-d]pyrimidine.

12. A compound in accordance with claim 1 which is: 1-(m-chlorophenyl)-3-methyl-2-oxo-1,2,3,4-tetrahydropyrido[2,3-d]pyrimidine.

13. A compound in accordance with claim 1 which is: 1-(m-chlorophenyl)-3-allyl-2-oxo-1,2,3,4-tetrahydropyrido[2,3-d]pyrimidine.

14. A compound in accordance with claim 1 which is: 1-(m-chlorophenyl)-3-methoxymethyl-2-oxo-1,2,3,4-tetrahydropyrido[2,3-d]pyrimidine.

15. A compound in accordance with claim 1 which is: 1-(p-chlorophenyl)-3-ethyl-2-oxo-1,2,3,4-tetrahydropyrido[2,3-d]pyrimidine.

16. A compound in accordance with claim 1 which is: 1-(m-bromophenyl)-3-ethyl-2-oxo-1,2,3,4tetrahydropyrido[2,3-d]pyrimidine.

17. A compound in accordance with claim 1 which is: 1-(m-bromophenyl)-3-propyl-2-oxo-1,2,3,4-tetrahydropyrido[2,3-d]pyrimidine.

18. A compound in accordance with claim 1 which is: 1-(m-trifluoromethylphenyl)-3-methyl-2-oxo-1,2,3,4-tetrahydropyrido[2,3-d]pyrimidine.

19. A compound in accordance with claim 1 which is: 1-(m-trifluoromethylphenyl)-3-ethyl-2-oxo-1,2,3,4-tetrahydropyrido[2,3-d]pyrimidine.

20. A compound in accordance with claim 1 which is: 1-(m-trifluoromethylphenyl)-3-isopropyl-2-oxo-1,2,3,4-tetrahydropyrido[2,3-d]pyrimidine.

21. A compound in accordance with claim 1 which is: 1-(m-trifluoromethylphenyl)-3-methoxymethyl-2-oxo-1,2,3,4-tetrahydropyrido[2,3-d]pyrimidine.

22. A compound in accordance with claim 1 which is: 1-(m-trifluoromethylphenyl)-3-carboxymethyl-2-oxo-1,2,3,4-tetrahydropyrido[2,3-d]pyrimidine.

23. A compound in accordance with claim 1 which is: 1-(3,4-dichlorophenyl)-3-ethyl-2-oxo-1,2,3,4-tetrahydropyrido[2,3-d]pyrimidine.

24. A compound in accordance with claim 1 which is: 1-(3,4-dichlorophenyl)-3-isopropyl-2-oxo-1,2,3,4-tetrahydropyrido[2,3-d]pyrimidine.

25. A compound in accordance with claim 1 which is: 1-(3,4-dichlorophenyl)-3-(2-fluoroethyl)2-oxo-1,2,3,4-tetrahydropyrido[2,3-d]pyrimidine.

26. A compound in accordance with claim 1 which is: 1-(m-nitrophenyl)-3-methyl-4-oxo-1,2,3,4-tetrahydropyrido(2,3-d)pyrimidine.

27. A compound in accordance with claim 1 which is: 1-(p-fluorophenyl)-3-ethyl-2-oxo-1,2,3,4-tetrahydropyrido(2,3-d)pyrimidine.

28. A compound in accordance with claim 1 which is: 1-(o-chlorophenyl)-3-methyl-2-oxo-1,2,3,4-tetrahydropyrido(2,3-d)pyrimidine.

29. A compound in accordance with claim 1 which is: 1-(o-chlorophenyl)-3-ethyl-2-oxo-1,2,3,4-tetrahydropyrido(2,3-d)pyrimidine.

30. A compound in accordance with claim 1 which is: 1-(m-trifluoromethylphenyl)-3-(2-hydroxyethyl)-2-oxo-1,2,3,4-tetrahydropyrido(2,3-d)pyrimidine.

* * * * *